(12) United States Patent
Cartlidge

(10) Patent No.: US 7,541,027 B2
(45) Date of Patent: Jun. 2, 2009

(54) USE OF AN EPITOPE OF VASCULAR ENDOTHELIAL GROWTH FACTOR RECEPTOR KDR/FLK-1

(75) Inventor: Sue Ann Cartlidge, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 133 days.

(21) Appl. No.: 10/507,164

(22) PCT Filed: Mar. 11, 2003

(86) PCT No.: PCT/GB03/00991

§ 371 (c)(1),
(2), (4) Date: Sep. 9, 2004

(87) PCT Pub. No.: WO03/078465

PCT Pub. Date: Sep. 25, 2003

(65) Prior Publication Data

US 2005/0221317 A1    Oct. 6, 2005

(30) Foreign Application Priority Data

Mar. 15, 2002 (GB) ................................. 0206072.1

(51) Int. Cl.
*A61K 39/395* (2006.01)
*A61K 38/04* (2006.01)
*G01N 33/53* (2006.01)
*C07K 4/12* (2006.01)
*C07K 16/28* (2006.01)

(52) U.S. Cl. ............... 424/130.1; 424/143.1; 424/185.1; 435/7.1; 435/70.21; 435/810; 530/327; 530/387.1; 530/388.22; 530/389.1

(58) Field of Classification Search ........................ None
See application file for complete search history.

(56) References Cited

U.S. PATENT DOCUMENTS 5,766,860 A * 6/1998 Terman et al. ................ 435/7.2
5,840,301 A * 11/1998 Rockwell et al. ......... 424/143.1
6,204,011 B1 * 3/2001 Kendall et al. ............. 435/69.1

FOREIGN PATENT DOCUMENTS

WO    WO 0229090    4/2002

OTHER PUBLICATIONS

Takahashi et al, EMBO J 20(11): 2768-2778, Jun. 2001.*
Stryer et al, in Biochemistry, Third edition, W H Freeman Company, New York, pp. 31-33, 1998.*
Kuby et al, Immunology, Second edition, pp. 85-96, 1994.*
Zhu et al, Investigational New Drugs 17: 195-212, 1999.*
Harlow et al, in Antibodies a Laboratory Manual, 1988, Cold Spring harbor laboratory publication, Cold Spring Harbor, NY, pp. 139-153.*
Wallace et al, in Methods in Enzymology 152: 432-439, 1987.*
Harlow et al, in Antibodies a Laboratory Manual, 1988, Cold Spring harbor laboratory publication, Cold Spring Harbor, NY, pp. 626-629.*
Clauss M (2000) Molecular biology of the VEGF and the VEGF receptor family Semin Thromb Hemost. 26(5)561-569.
Cullinan-Bove K et al. (1993) Vascular endothelial growth factorvascular permeability factor expression in the rat uterus rapid stimulation by estrogen correlates with estrogen-induced increases in uterine capillary permeability and growth Endocrinology 133 829-837.
Cunningham SA et al. (1997) Interactions of FLT-1 and KDR with phospholipase C gamma. Indentification of the phosphotyrosine binding sites Biochem. Biophys. Res. Comm. Biochem. Biophys. Res. Comm. 240635-639.
Dougher M et al. (1999) Autophosphorylation of KDR in the kinase domain is required for maximal VEGF-stimulated kinase activity and receptor internalization Oncogene 18(8)1619-1627.
Fan TP et al. (1995) Controlling the vasculature angiogenesis, anti-angiogenesis and vascular targeting of gene therapy Trends Pharmacol Sci. 16(2)57-66.
Folkman J (1995) Angiogenesis in cancer, vascular, rheumatoid and other disease Nature Medicine. 1(1)27-31.
Karkkainen MJ et al. (2000) Vascular endothelial growth factor receptors in the regulation of angiogenesis and lymphangiogenesis Oncogene 195598-5605.
Kendall RL et al. (1999) Vascular Endothelial Growth Factor Receptor KDR Tyrosine Kinase Activity Is Increased by Autophosphorylation of Two Activation Loop Tyrosine Residues J Biol Chem 274(10)6453-6460.
McMahon G (2002) VEGF receptor signaling in tumor angiogenesis Oncologist. 5 Suppl 13-10.
Ratcliffe KE et al. (2002) Sck is expressed in endothelial cells and participates in vascular endothelial growth factor-induced signaling Oncogene 21(41)6307-6316.
Senger DR et al. (1993) Vascular Permeability Factor (VPF, VEGF) in Tumor Biology Cancer Met Reviews 12303-324.
Terman BI et al. (1991) Identification of a new endothelial cell growth factor receptor tyrosine kinase. Oncogene 61677-1683.
Terman BI et al. (1992) Identification of the KDR tyrosine kinase as a receptor for vascular endothelial cell growth factor Biochem Biophys Res Commun. 187(3)1579-1586.
Warner AJ et al. (2000) The Shc-related adaptor protein, Sck, forms a complex with the vascular-endothelial-growth-factor receptor KDR in transfected cells Biochem J. 347(Pt2)501-509.

(Continued)

*Primary Examiner*—Phuong Huynh
(74) *Attorney, Agent, or Firm*—Morgan Lewis & Bockius LLP

(57) ABSTRACT

The present invention relates to the use of the epitope which comprises the tyrosine at position 1214 in the amino acid sequence of the vascular endothelial growth factor receptor, KDR/Flk-1, as a marker in the measurement of a change in the activation state of the KDR/Flk-1 receptor and to probes, such as antibodies, which recognize said epitope. The invention also relates to the use of KDR/Flk-1 epitope Y1214 as a marker in the detection of and/or measurement of the level of the KDR/Flk-1 receptor and to assays which utilize the use of the Y1214 epitope and to compounds derived from said assays.

13 Claims, 1 Drawing Sheet

OTHER PUBLICATIONS

Figure 1:
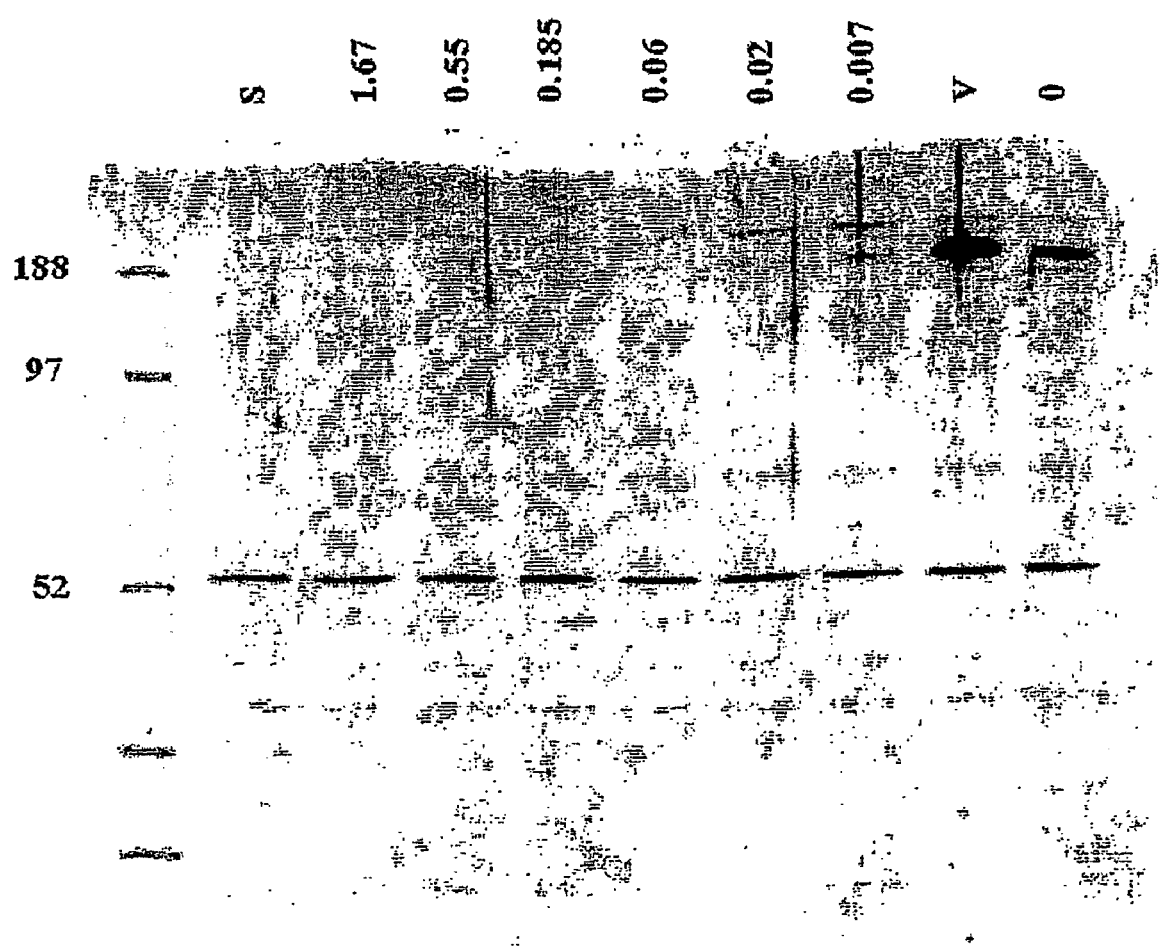

Zeng H (2001) Tyrosine Residues 951 and 1059 of Vascular Endothelial Growth Factor Receptor-2 (KDR) Are Essential for Vascular Permeability Factor Vascular Endothelial Growth Factor-induced Endothelium Migration and Proliferation, Respectively J. Biol. Chem. 276(35)32714-32719.

Wood et al. (2000) "PTK787/ZK 222584, a novel and potent inhibitor of vascular endothelial growth factor receptor tyrosine kinases, impairs vascular endothelial growth factor-induced responses and tumor growth after oral administration" Cancer Res. 60(8):2178-2189.

Igarashi et al. (1998) "Tyrosine 1213 of Flt-1 Is a Major Binding Site of Nck and SHP-2" Biochemical and Biophysical Research Communications 246(1): 95-99 (p. 98, right-hand col., last paragraph-p.99; figs. 2-4).

Carroll et al. (1999) "KDR activation in astrocytic neoplasms" Cancer 86(7): 1335-1341 (Abstract).

Menrad et al. (1997) "Novel antibodies directed against the extracellular domain of the human VEGF-receptor type II" Hybridoma 16(5): 465-471 (Abstract, p. 469).

Zhu et al. (1999) "Inhibition of vascular endothelial growth factor induced mitogenesis of human endothelial cells by a chimeric anti-kinase insert domain-containing receptor antibody" Cancer Letters 136(2): 203-213 (Abstract, p. 210, left-hand col., last paragraph—right-hand col.).

Rockwell et al. (1995) "In-vitro neutralization of vascular endothelial growth factor activation of flk-1 by a monoclonal antibody" Mol. Cell. Diff. 3(1): 91-109 (p. 102, paragraphs 2,3, abstract).

Meyer et al. (2002) "The Presence of a Single Tyrosine Residue at the Carboxyl Domain of Vascular Endothelial Growth Factor Receptor-2/FLK-1 Regulates Its Autophosphorylation and Activation of Signaling Molecules" J. Biol. Chem., 277(30): 27081-27087 (Abstract, figs. 1, 4-6).

Wood et al., Cancer Research, vol. 60, No. 8, Apr. 15, 2000, pp. 2178-2189, XP000971163, ISSN: 0008-5472, abstract.

Igarashi Katsuhide et al., Biochemical and Biophysical Research Communications, vol. 246, No. 1, May 8, 1998, pp. 95-99, XP002251094, ISSN: 0006-291X, p. 98, right-hand col., last paragraph-p. 99; figs. 2-4.

Carrol Rona et al., Cancer, vol. 86, No. 7, Oct. 1, 1999, pp. 1335-1341, XP002251095, ISSN: 0008-543X, abstract.

Takahashi et al,. The Embo Journal, England, vol. 20, No. 11, Jun. 1, 2001, pp. 2768-2778, XP002251096, ISSN: 0261-4189, cited in application, abstract, fig. 1, pp. 2769, left-hand col., para. 1.

Menrad et al., Hybridoma, vol. 16, No. 5, Oct. 1, 1997, pp. 465-471, XP002052460, ISSN: 0272-457X, abstract, p. 469.

Zhu et al., Cancer Letters, vol. 136 No. 2, Mar. 1, 1999, p[p. 203-213, XP002251097, ISSN: 0304-3835, abstract, p. 210, left-hand col., last paragraph—right-hand col.

Rockwell et al., Mollecular and Cellular Differentiation, vol. 3, No. 1, 1995, pp. 91-109, XP002052455, ISSN: 1065-3074, p. 102, paragraphs 2,3, abstract.

Meyer et al., Journal of Biological Chemistry, vol. 277, No. 30, May 22, 2002, pp. 27081-27087, XP002251098, Jul. 28, 2002, ISSN: 0021-9258, abstract, figs. 1, 4-6.

* cited by examiner

USE OF AN EPITOPE OF VASCULAR ENDOTHELIAL GROWTH FACTOR RECEPTOR KDR/FLK-1

The present invention relates to the use of the Y1214 epitope of the KDR/Flk-1 receptor as a marker in the measurement of a change in the activation state of the KDR/Flk-1 receptor. The invention also relates to the use of the KDR/Flk-1 epitope Y1214 as a marker in the detection of and/or measurement of the level of the KDR/Flk-1 receptor and to assays which utilise the use of the Y1214 epitope and to compounds derived from said assays.

KDR/Flk-1 is one of the receptors which binds vascular endothelial growth factor (VEGF), a growth factor which is engaged in the processes of angiogenesis. Three receptors have been identified which bind VEGF, VEGFR-1 (also known as Flt-1), VEGFR-2 (also known as KDR or Flk-1) and VEGFR-3 (also known as Flt-4). For more information on the receptors bound by VEGF the reader is referred to the following review articles: Clauss, 2000 Seminars in Thrombosis and Hemostasis 26: 561-569; McMahon 2000, The Oncologist 5: 3-10; and Karkkainen & Petrova, 2000, Oncogene 19: 5598-5605.

Normal angiogenesis plays an important role in a variety of processes including embryonic development, wound healing and several components of female reproductive function. However, angiogenesis is also involved in a number of disease conditions. For example, undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). VEGF also has effects on vascular permeability, which is thought to play a role in both normal and pathological physiological processes (Cullinan-Bove et al, 1993, Endocrinology 133: 829-837; Senger et al, 1993, Cancer and Metastasis Reviews, 12: 303-324).

The observation that angiogenesis is involved in a number of disease conditions has led to a number of approaches being undertaken to treat diseases by the modulation of angiogenesis. One of these approaches has been to develop inhibitors of the activity of receptors which bind VEGF. VEGF receptors belong to a family of receptors, called receptor tyrosine kinases (RTKs). RTKs are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. (For a review of RTKs, the reader is referred to: Schlessinger, 2000, Cell, 103:211-255. Examples of inhibitors of the VEGF receptor tyrosine kinase (VEGF RTK) can be found in the following patent applications: International Application, Publication Number WO97/42187 and International Application, Publication Number: WO98/13350.

In addition to the need for inhibitors of the VEGF RTK, there is also a need for tools to characterise the activation and deactivation of the VEGF RTK. Such tools would be useful, for example, in studies characterising the biochemistry of the VEGF RTK and in the measurement of changes in the activation state of the VEGF RTK during clinical studies of inhibitors of the receptor, thus giving an indication of the therapeutic efficacy of said inhibitors.

One approach to the development of such tools is to look for amino acid epitopes on the VEGF receptor which are phosphorylated during activation of the VEGF RTK. Such epitopes could be used, for example, in following the activation and de-activation states of the VEGF RTK Takahashi et al, 2001, EMBO Journal 20: 2768-2778 have identified two epitopes on the KDR/Flk-1 sub-type of the VEGF receptor, these are the tyrosine residues located at positions 1175 and 1214 in the amino acid sequence of the KDR/FLk-1 receptor (referred to hereafter as Y1175 and Y1214 respectively). In this paper the authors characterised these two epitopes and observed that Y1175 but not Y1214 was a major phospholipase C-gamma (PLCγ) binding site linked to activation of MAP kinase, an important protein downstream of the biochemical pathways which is indirectly activated by binding of VEGF to the KDR/Flk-1 receptor. Thus, the authors concluded that Y1175 but not Y1214 plays a crucial role in the transduction of signals from the KDR/Flk-1 receptor to the MAP kinase pathway and DNA synthesis in endothelial cells. Thus, teaching that Y1175, but not Y1214, would be an important marker for following activation of the KDR/Flk-1 receptor. We have raised antibodies against the Y1214 epitope and surprisingly found that we could use this epitope to follow activation of the KDR/Flk-1 receptor, observing inhibition of the phosphorylation of Y1214 by inhibitors of the KDR/Flk-1 RTK (as shown in FIG. 1 below). We have also found that inhibitors of the KDR/Flk-1 RTK also inhibit phosphorylation of MAP Kinase in parallel with inhibition of the phosphorylation of the Y1214 epitope. Thus, surprisingly we have found that Y1214 is an important marker for following the activation of the KDR/Flk-1 receptor.

Thus, according to the first aspect of the present invention there is provided the use of the KDR/Flk-1 epitope Y1214 as a marker in the measurement of a change in the activation state of the KDR/Flk-1 receptor.

The Y1214 epitope could be used to detect the presence of the KDR/Flk-1 receptor in biological samples and to measure the levels of the KDR/Flk-1 receptor in biological samples. Thus, according to a further feature of the first aspect of the invention there is provided the use of the KDR/Flk-1 epitope Y1214 as a marker in the detection of and/or measurement of the level of the KDR/Flk-1 receptor.

One approach to allow such detection and/or measurement of the KDR/Flk-1 receptor is to develop probes to the Y1214 epitope, these could be developed to either the phosphorylated or de-phosphorylated epitope. Thus, according to a second aspect of the invention there is provided a probe directed to the KDR/Flk-1 epitope Y1214. Examples of such probes include binding proteins such as antibodies.

According to a further feature of the second aspect of the invention there is provided an antibody which specifically binds to epitope Y1214. A peptide fragment of the KDR/Flk-1 receptor comprising the Y1214 epitope may be utilized to prepare antibodies that specifically bind to Y1214. A specific example of such antibody preparation is described in Example 1 herein.

Polyclonal antibodies can be readily generated from a variety of sources, for example, horses, cows, goats, sheep, dogs, chickens, rabbits, mice or rats, using procedures that are well-known in the art. In general, a peptide comprising the Y1214 epitope is administered to the host animal typically through parenteral injection. The immunogenicity of a peptide comprising the Y1214 epitope may be enhanced through the use of an adjuvant, for example, Freund's complete or incomplete adjuvant. Following booster immunizations, small samples of serum are collected and tested for reactivity to the Y1214 epitope. Examples of various assays useful for such determination include those described in: *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay, radioimmunoprecipitation, enzyme-linked immuno-sorbent assays (ELISA), dot blot assays, and sandwich assays, see U.S. Pat. Nos. 4,376,110 and 4,486,530.

Monoclonal antibodies may be readily prepared using well-known procedures, see for example, the procedures described in U.S. Pat. Nos. RE 32,011, 4,902,614, 4,543,439 and 4,411,993; Monoclonal Antibodies, Hybridomas: *A New Dimension in Biological Analyses*, Plenum Press, Kennett, McKearn, and Bechtol (eds.), (1980), each of which is incorporated herein by reference.

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3: 1-9 (1990) each of which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7: 394 (1989), which is incorporated herein by reference. Monoclonal antibodies can also be produced using cell lines, such as CHO cells or NS0 cells, or micro-organisms, such as bacteria or yeast, into which the genes for the heavy and light chains of the antibody have been transfected. Examples of such methods can be found in U.S. Pat. Nos. 6,331,415, 5,876,961, 5,545,403 and 5,807,715, each of which is incorporated by reference.

Thus, according to a further aspect of the invention there is provided a monoclonal antibody which specifically binds to the KDR/Flk-1 epitope Y1214.

According to a further aspect of the invention there is a provided a hybridoma which produces an antibody which specifically binds to the KDR/Flk-1 epitope Y1214, preferably a monoclonal antibody.

According to a further aspect of the invention there is provided a recombinant cell line transfected with the cDNA for the expression of the heavy and light chains for an antibody which specifically binds to the KDR/Flk-1 epitope Y1214.

Once isolated and purified, the antibodies against Y1214 may be used to detect the presence of Y1214 in a sample using established assay protocols. In addition such antibodies could be used to measure the levels of the KDR/Flk-1 receptor in samples. Further, the antibodies of the invention may be used therapeutically to bind to the Y1214 epitope and inhibit its activity in-vivo.

Thus, according to a further aspect of the invention there is provided the use of an antibody which binds to the KDR/Flk-1 epitope Y1214 in the manufacture of a medicament, preferably a medicament for the treatment of cancer.

According to a further aspect of the invention there is provided a method of treatment using an antibody which binds to the KDR/Flk-1 epitope Y1214, preferably a method for the treatment of cancer.

Another approach to the use of the KDR/Flk-1 epitope Y1214 as a marker in the measurement of a change in the activation state of the KDR/Flk-1 receptor is to measure the phosphorylation state of the KDR/Flk-1 receptor activated in the presence of adenosine triphosphate labelled with radioactive phosphate (for example, labelled with phosphorous 32) and to determine the level of radioactivity of the KDR/Flk-1 receptor, preferably the level of radioactivity in peptide fragments of the KDR/Flk-1 receptor comprising Y1214.

A further approach to the use of the KDR/Flk-1 epitope Y1214 as a marker in the measurement of a change in the activation state of the KDR/Flk-1 receptor is to use nuclear magnetic resonance (NMR) to follow changes in the phosphorylation state of Y1214.

According to a further aspect of the invention there is provided a method of generating a probe directed to the Y1214 epitope of the KDR/Flk-1 receptor. Preferably the generation of an antibody.

According to a further aspect of the invention there is provided a method of generating an antibody, which comprises:

(i) immunizing a mammal with a peptide which comprises the KDR/Flk-1 epitope Y1214; and
(ii) isolating an antibody from said mammal.

The skilled man would have access to a large number of assay techniques with which to develop assays to detect, measure the levels of, and/or measure a change in the activation state of the KDR/Flk-1 receptor, based on the knowledge of the importance of the Y1214 epitope. Examples of such assay techniques include, fluorimetic assays, chromogenic assays, radiolabelled assays or chemiluminescence assays. Thus, according to a third aspect of the invention there is provided an assay method to detect, measure the levels of, and/or measure a change in the activation state of the KDR/Flk-1 receptor utilising Y1214 as a marker, preferably to measure a change in the activation state of the KDR/Flk-1 receptor.

For guidance for the design of biological assays the skilled man will be aware of a number of standard works. Examples of such standard works include: Knight (1995) Fluorimetric Assays of Proteolytic Enzymes, Methods in Enzymology 248, 18-34; Chard (1978) An Introduction to Radioimmunoassay and related techniques, Elsevier/North-Holland Biomedical Press; and Basic Methods in Molecular Biology. First author Leonard G Davis. 1986 Elsevier Science Publishing Co. Inc., Amsterdam.

According to a further feature of the third aspect of the invention there is provided an assay method for the measurement of a change in the activation state of the KDR/Flk-1 receptor, comprising (a) mixing a biological sample with an assay mixture comprising one or more probes directed to the KDR/Flk-1 epitope, Y1214; and
(b) measuring a signal which is proportional to the proportion of the KDR/Flk-1 epitope, Y1214 which is in the phosphorylated or un-phosphorylated state.

According to a further feature of the third aspect of the invention there is provided an assay method for the measurement of a change in the activation state of the KDR/Flk-1 receptor, comprising (a) mixing a biological sample with an assay mixture comprising one or more probes directed to the KDR/Flk-1 epitope, Y1214; and
(b) measuring the activation state of the KDR/Flk-1 receptor in the biological sample.

According to a fourth aspect of the invention there is provided a diagnostic kit to detect, measure the levels of, and/or measure a change in the activation state of the KDR/Flk-1 receptor comprising reagents for preparing an assay mixture comprising a probe of the invention and instructions for use thereof. Preferably said diagnostic kit is directed towards measuring the activation state of the KDR/Flk-1 receptor.

According to a further feature of the fourth aspect of the invention there is provided a diagnostic kit to detect, measure the levels of, and/or measure a change in the activation state of the KDR/Flk-1 receptor in a biological sample, for use with a method of the invention, the diagnostic kit comprising reagents for preparing an assay mixture and instructions for use thereof.

According to a further feature of the fourth aspect of the invention there is provided a method of determining the effective dose of an inhibitor of the KDR/Flk-1 receptor, which comprises:
(a) dosing one or more humans or other mammals with a range of KDR/Flk-1 receptor inhibitor concentrations, preferably one or more humans;
(b) isolating a biological sample from said humans or other mammals, preferably a cell sample;
(c) measuring a signal proportional to the activation state of the KDR/Flk-1 receptor using an assay method of the invention; and
(d) calculating the effective dose of the inhibitor from the measured signal.

It would be clear to the skilled man that the KDR/Flk-1 receptor inhibitor is an inhibitor of the activation of the KDR/Flk-1 receptor by binding of a ligand, such as VEGF, to the receptor. This could occur at the VEGF binding site or at an allosteric site. Such inhibitors include inhibitors of the KDR/Flk-1 receptor tyrosine kinase or agents which blocks binding of ligands to the receptor, for example antibodies directed to the KDR/Flk-1 receptor. A preferred inhibitor is N-(4-bromo-2-fluorophenyl)-6-methoxy-7-[(4-methylpiperidin-1-yl)methoxy]quinazolin-4-amine.

According to a further feature of the fourth aspect of the invention there is provided a method of determining the effective therapeutic dose of a KDR/Flk-1 receptor inhibitor which comprises:
(a) dosing one or more humans or other mammals with a range of KDR/Flk-1 receptor inhibitor concentrations, preferably one or more humans;
(b) isolating a biological sample from said humans or other mammals, preferably a cell sample;
(c) measuring the activation state of the KDR/Flk-1 receptor using a method of the invention; and
(d) calculating the effective therapeutic dose of the inhibitor from the measured activation state.

According to a the fifth aspect of the invention there is provided a method of preparing a pharmaceutical composition of a KDR/Flk-1 receptor inhibitor which comprises:
(a) determining the effective dose of the inhibitor according to a method of the invention; and
(b) preparing a unit dose of inhibitor comprising an amount of inhibitor within the effective dose range and a pharmaceutically acceptable excipient.

According to a further feature of the fifth aspect of the invention there is provided a method of preparing a pharmaceutical composition which comprises:
(a) determining the effective therapeutic dose of a KDR/Flk-1 receptor inhibitor by a method of the invention, and
(b) mixing the inhibitor in an amount within the effective therapeutic dose range with a pharmaceutically acceptable excipient.

According to a further feature of the fifth aspect of the invention there is provided a pharmaceutical composition prepared by one of the above methods of preparing a pharmaceutical composition.

According to a sixth aspect of the invention there is provided a method of determining whether a chemical compound is an in-vivo inhibitor of the KDR/Flk-1 receptor tyrosine kinase activity which comprises, measuring the degree of phosphorylation of Y1214 in a biological sample obtained from a subject to whom said chemical compound has been administered.

According to a seventh aspect of the invention there is provided the use of the degree of phosphorylation of Y1214 as a surrogate marker of KDR/Flk-1 receptor tyrosine kinase inhibitory activity of a chemical compound.

The skilled man will appreciate that this effective therapeutic dose may be formulated in one or more preparations to be delivered to the patient over a defined period of time. The skilled man will also appreciate that once the effective dose has been determined further pharmaceutical compositions can be prepared which will have been indirectly prepared by the above methods.

Within this specification the following terms are defined as follows:

"Activation state"—any change in the molecular conformation of the KDR/Flk-1 receptor which leads to the direct or indirect modulation of the activity of another protein or other proteins within the cell membrane or any other part of a animal or human cell. Preferably the change in conformation is induced directly or indirectly by the phosphorylation of one or more amino acid residues within the KDR/Flk-1 receptor.

"Antibodies" include polyclonal antibodies, monoclonal antibodies, and the various types of antibody constructs such as for example $F(ab')_2$, Fab and single chain Fv. Antibodies are defined to be specifically binding if they bind Y1214 with a $K_c$ of greater than or equal to about $10^7$ $M^{-1}$. Affinity of binding can be determined using conventional techniques, for example those described by Scatchard et al., *Ann N.Y. Acad. Sci.*, 51:660 (1949).

"Assay Mixture"—comprises reagents suitable for the detection, measurement of the levels of, and/or measurement of a change in the activation state of the KDR/Flk-1 receptor; such reagents are readily selectable by a person skilled in the art. For example, a preferred assay mixture comprises a suitable buffer, one or more labelled probes directed to the KDR/Flk-1 epitope, Y1214, and optionally any other co-factors which may be required.

"Biological sample" is a sample of material derived from any component of an animal body. Such material includes, but is not limited to, blood, urine, tissue sections, and tissue biopsies, preferably tissue biopsies or blood. Tissue biopsies may be assayed as sections or may be assayed as a cell suspension. Biological samples may be derived from a variety of animal species, preferably mammals, more preferably human, monkey, dog, guinea pig, rat or mouse, further preferably rat, mouse or human, most preferably human. The skilled man would appreciate that a biological sample may be purified or partially purified before use. "Biological sample' also includes cultured cell lines, and material derived therefrom. A preferred biological sample is a needle biopsy from a tumour.

"Effective Dose"—for the avoidance of doubt effective dose means the effective therapeutic dose for the treatment of a disease wherein inhibition of the activity of the KDR/Flk-1 receptor would be of therapeutic benefit. The skilled man would be able to calculate the effective therapeutic dose from the degree of inhibition of the activity of the KDR/Flk-1 receptor in the biological sample.

"KDR/Flk-1 epitope Y1214"—for the avoidance of doubt, references to the KDR/Flk-1 epitope Y1214 relate to the epitope in both its un-phosphorylated and phosphorylated form.

"Modulation"—for the avoidance of doubt modulation can relate to either an increase in activity or a decrease in activity.

"Probe"—relates to any moiety which specifically binds to an amino acid sequence, for example a sequence containing the Y1214 epitope of the KDR/Flk-1 receptor.

"Signal"—for the avoidance of doubt a signal could be derived from a single probe or could be a number of signal-derived from two or more probes. For example, a probe directed to the phosphorylated epitope could be used in combination with a probe directed to the un-phosphorylated epitope and the resulting 2 signals be used to measure the proportion of receptor in the phosphorylated and un-phosphorylated state.

"Surrogate marker"—relates to any measurement of a biological or biochemical activity which indirectly indicates the efficacy of a chemical compound on the treatment of a disease state in an animal, preferably a human.

"Y1214"—relates to the tyrosine residue located at position 1214 in the amino acid sequence of the mature KDR/Flk-1 receptor. The sequence is set out in Terman et al 1991, Biochem Biophys Research Commun 187(3), 1579-1586. In the Terman et al sequence the initiator methionine is present, thus Y1214 is shown at position 1215 of the sequence. This methionine would be absent in the transcribed protein; thus the tyrosine residue relating to the present invention would be present at position 1214. The sequence of KDR/Flk-1 can also be found at SwissProt Accession No. P35968.

The invention will now be illustrated with reference to the following non-limiting examples and accompanying figure, wherein:

FIG. 1: shows a dose dependent decrease in phosporylation of the Y1214 eptitope in response to increasing concentration of the KDR receptor tyrosine kinase inhibitor 4-[(4-fluoro-2-methyl-1H-indol-5-yl)oxy]-6-methoxy-7-(3-piperidin-1-yl-propoxy)quinazoline; where lane O=untreated HUVEC cell lysate, lane V=VEGF-treated HUVEC cell lysate and the remaining lanes show the effect of 0.007-5.0 uM compound on VEGF-treated cells. The arrow shows the position of KDR on the membrane.

and the following abbreviations are used:
PBST—0.05% Tween-20 in PBS.
BSA—bovine serum albumin;
HUVECs—human unbilical vein endothelial cells
PBS—phosphate-buffered saline; and
OVA—ovalbumin

EXAMPLE 1

Preparation of Polyclonal Antibodies Directed to the KDR/Flk-1 Epitope, Y1214

Conjugation of KDR/Flk-1 Peptide to OVA Using Maleimide
KDR/Flk-1 peptide "Ac-CDPKFHY(p)DNTAGIS-NH$_2$" (SEQ ID NO: 1) was dissolved in PBS (0.1M pH=7.4) at a concentration of 1 mg/ml and freeze-dried maleimide activated ovalbumin (ex Pierce & Warriner Cat. No. 77126) was dissolved in PBS at 1 ml/mg. 3 mls of peptide was then mixed with 3 mls of maleimide-activated OVA and left to react for 4 hours at room temperature in the dark, with continuous mixing on a roller. After 4 hours the reaction mixtures were dialysed against 10 liters of stirred PBS overnight at 4° C. (10000 molecular weight cut off). After dialysis the volumes of the reaction mixtures were adjusted to give final protein concentration of 1 mg/ml. 200 μl aliquots were then stored at −20° C.

Immunisation of Rabbits with KDR/Flk-1 Peptide Conjugate

Three female New Zealand White rabbits were immunised with the ovalbumin conjugate of the KDR/Flk-1 peptide. Immunisations were carried out using the subcutaneous route, each dose being delivered to 4 sites on the back of the rabbit, in a total volume of 1 ml. Four doses were given at four weekly intervals, with each dose containing 50 μgs of conjugate, as follows.

Dose 1—delivered as an emulsion, made up using a 1:1 mixture of PBS and Freunds Complete Adjuvant;

Dose 2—delivered as an emulsion, made up using a 1:1 mixture of PBS and Freunds Incomplete Adjuvant;

Dose 3—delivered as an emulsion, made up using a 1:1 mixture of PBS and Freunds Incomplete Adjuvant; and Dose 4—delivered in PBS alone.

Pre-bleeds were taken prior to the first dose and 10 days after each subsequent dosing. The blood was removed from the marginal ear vein of the animal, allowed to clot for several hours at room temperature and then stored at 4° C. overnight. The samples were then spun in a bench-top centrifuge for 15-30 minutes and the serum decanted from the pellet. The serum samples were then frozen and stored at −20° C.

Assay of Test Bleeds from Rabbits Immunised with Phosphorylated Peptide

| | | |
|---|---|---|
| Phosphorylated | [Ac-CDPKFHY(p)DNTAGIS-NH$_2$] | (SEQ ID NO: 1) |
| Non Phosphorylated | [Ac-CDPKFHYDNTAGIS-NH$_2$] | (SEQ ID NO: 2) |

Assay were performed on 96 well polystyrene plates. Plates were coated with either phosphorylated or non-phosphorylated peptide at 2 μg/ml in bicarbonate buffer (0.1M, pH 9.6) and incubated for 8 hrs at room temperature. Plates were then washed once with PBS/Tween 20 (0.5%)(pH=7.4) and blocked with a 1% solution of dried, skimmed milk powder in PBS at 120 μl/well overnight at 4° C.

Test bleeds were then assayed as follows. Plates were then washed once with PBS/Tween20 (0.5%)(pH7.4), samples added to wells at 100 μl/well; doubling dilutions, starting with neat serum, in duplicate and then incubated for 3 hours room temperature. Plates were then washed three times with PBS/Tween20 (0.5%)(pH7.4) and a peroxidase labelled Goat anti Rabbit antibody (Sigma Chemical Co, Poole, Dorset, UK Catalogue Number A-0545) diluted to 1 in 4000 with PBS/Tween20 (0.5%)(pH7.4) was added at 100 μl/well. Plates were then incubated for 3 hours at room temperature. Plates were then washed four times with PBS/Tween20 (0.5%)(pH7.4). Then, peroxidase substrate, 600 μg/ml ortho-phenylene-diamine+0.02% urea H$_2$O$_2$ (in citrate phosphate pH 5) substrate was added at 100 μl/well to the plates and incubated at room temperature. The reaction was stopped after 15 minutes by the addition of 0.1M citric acid at 50 μl/well.

Plates then read at 450 nm using a spectrophotometric plate reader.

Preparation of Phosphorylated KDR/Flk-1 Peptide and Non-Phosphorylated KDR/Flk-1 Peptide Affinity Columns Using "Sulfolink™"

Sulfolink™ is a 6% cross-linked beaded agarose gel with immobilised iodoacetyl groups for immobilising sulfhydryl-containing peptides. (Source: Pierce Chemical Company, Rockford, Ill., USA).

10 mls of "Sulfolink" slurry was added to a disposable 5 ml (bed volume) polypropylene columns with additional reservoir fitted at room temperature and allowed to sediment for 2 hours. The column was then washed twice with 25 mls of 50 mM Tris+5 mM Na-EDTA pH 8.5. Peptides were dissolved at 1 mg in 5 mls of Tris/EDTA (as above).

Affinity columns were prepared by adding a 5 ml solution of either the phosphorylated or non-phosphorylated peptide, the columns were then mixed well using a long needle, capped and mixed on shaker for 15 minutes. After 15 minutes columns were set upright and left to settle for 30 minutes. Then columns were drained and 6 mls of 50 mM Cysteine in Tris/EDTA run into each column. The columns were then capped, mixed thoroughly with needle, and mixed for 15 minutes. Column were then set upright and allowed to settle for 30 minutes. 40 mls of 1M NaCl was then run through each column, followed by 30 ml 0.05% Sodium Azide. Columns were then stored at 4° C.

Purification of Antibodies Using Non-Phosphorylated Peptide and Phosphorylated Peptide Affinity Columns Prior to column chromatography serum samples were purified by precipitation using 50% ammonium sulphate. The precipitates were resuspended in approximately 10 mls of PBS and dialysed against 10 Litres of PBS overnight at 4° C. (10,000 molecular weight cut off). The ammonium sulphate-purified samples were then further purified by chromatography on a phosphorylated peptide affinity column followed by chromatography on a non-phosphorylated peptide column. Prior to use affinity columns prepared as described above with phosphorylated or non-phosphorylated peptide were brought to room temperature and washed with 20 mls of PBS.

Column chromatography was performed as follows.

(i) Phosphorylated Peptide Affinity Column 10 mls of ammonium sulphate purified material was made up to 50 mls with PBS and added to the top of a phosphorylated peptide affinity column and allowed to run through, then the column was washed with 15 mls of PBS. The column was then eluted with approximately 10 mls of 100 mM Glycine pH 3.0 and 10×1 ml fractions were collected, with 100 µl of 1M Tris pH 8.9 being added to collection vials from fraction 4-10. The elution from the column was checked by measuring the optical density of the fraction at 280 nm in a spectrophotometer. The column was then regenerated by the addition of 10 ml 100 mM Glycine pH 2.5, followed by 20 mls PBS and the column was stored at 4° C.

(ii) Non-Phosphorylated Peptide Affinity Column

Fractions 3-8 were pooled and added to the non-phosphorylated peptide column, followed by 10 mls of PBS. All material coming through the column was collected in 1 ml fractions and the optical density at 280 nm measured checked on a spectrophotometer. Fractions 2-7 were then pooled and dialysed against PBS, overnight at 4° C. After dialysis, the samples were stored at 4° C. for immediate use, or at −20° C. for storage.

Assay of Rabbit Fractions from Phosphorylated Peptide and Non-Phosphorylated Peptide Affinity Columns 96 well plates were coated for 4 hours at room temperature with 2 µg/ml of peptide in 0.1M bicarbonate buffer pH 9.6. The plates were then washed once with PBS/Tween20 (0.5%) (pH=7.5) and blocked with a 1% solution of dried, skimmed milk powder at 200 µl/well for 1 hour at room temperature. Plates were then washed once with PBS/Tween20 (0.5%) (pH7.5) and samples added to wells at 100 µl/well. Fractions were assayed in doubling dilutions, starting at 25 ug/ml of protein (by optical density at 280 nm). Plates were then incubated at 4° C. overnight.

Next morning plates were washed three times with PBS/Tween20 (0.5%)(pH7.5) and a goat anti-rabbit peroxidase antibody (Sigma Chemical Co, Poole, Dorset, UK, Catalogue Number:A-0545) diluted to 1 in 2000 with PBS/Tween20 (0.5%)(pH7.5) was added at 100 µl/well. Plates were then incubated for 4 hours at 4° C. After 4 hours plates were washed four times with PBS/Tween20 (0.5%)(pH7.5). Then, the peroxidase substrate ortho-phenylene diamine+urea $H_2O_2$ (in citrate phosphate buffer pH=5) at 100 ul/well was added. After 3 minutes the reaction was stopped by addition of 0.1M Citric acid 100 ul/well. Plates were then read at 450 nm on a spectrophotometric plate reader.

EXAMPLE 2

Treatment of Human Umbilical Vein Endothelial Cells (HUVECs) with Inhibitors of KDR/Flk-1 Receptor Tyrosine Kinase HUVECs were obtained from TCS Cellworks, Buckingham, UK (Catalogue number ZHS 8965) and cultured in Large Vessel Endothelial Cell Basal Medium+recommended supplements obtained from TCS Cellworks (catalogue numbers ZHM 2951 and ZHS 8965). Cells were used when close to confluence in 3×75 $cm^2$ tissue culture flasks. Prior to treatment with inhibitor cells were cultured overnight in Basal Medium without supplements.

HUVECS were treated with inhibitors as follows. Inhibitors were diluted in Basal Medium, added to cultures at a final concentration of 1 µM. and the cells incubated at 37° C. for 82 minutes. After 82 minutes 50 ng/ml VEGF was added to the cells and the cells incubated for a further 8 minutes at 37° C. After this further incubation the culture medium was removed from the cells and the cells lysed with 2.5 ml sample buffer [Sample buffer: 4 parts NuPage sample buffer (Novex, NP0007, Invitrogen, Paisley, Scotland) to 1 part distilled water]. The lysate was collected, 3 µl of β-mercaptoethanol added and heated to 95° C. for 10 minutes to ensure complete reduction and denaturation. The lysates can be stored at −20° C. until analysed.

EXAMPLE 3

SDS PAGE of Lysates

Lysates were analysed using SDS polyacrylamide gel electrophoresis (PAGE) to separate the proteins within the lysates. Electrophoresis was performed using a 4-12% NuPage bis-tris gel (Invitrogen, Paisley, Scotland, UK, catalogue no. NP0321) and NUPAGE MOPS SDS Running Buffer (Invitrogen, Paisley, Scotland, UK, catalogue no. NP0001). After the electrophoresis the protein were transferred from the gels to nitrocellulose membrane using Novex blotting modules as per the manufacturers instructions (Invitrogen, Paisley, Scotland, UK, catalogue no. LC2001). The membranes were then stained with Ponceau S (Sigma, Poole, Dorset, UK. Catalogue No. P-7170) and store air-dried, in sealed bags at 4° C.

EXAMPLE 4

Treatment of Nitrocellulose Membranes with Anti-KDR/Flk-1 Antibodies

Nitrocellulose membranes were incubated for 1 hour in 5% solution of dried, skimmed milk powder in PBST [Marvel/PBST] at room temperature. After 1 hour the membrane was incubated for between 2-3 hours at room temperature with an anti-KDR/Flk-1 antibody diluted 1:100 in Marvel/PBST. After this period the membrane was washed four times for at least 5 minutes with PBST and then the membrane was incubated with an appropriate secondary antibody (e.g. NEB an anti-rabbit antibody bound to horse-radish peroxidase; used at a dilution of 1:2000) for 1 hour at room temperature. The membrane was then washed for 30 minutes using at least 4 changes of PBST, incubated with Lumiglo reagents (Cell Signaling Technology Inc, Cummings Center, Beverly, Mass. USA) as directed. The membranes were then exposed to X-ray film and the film developed to reveal the bands reactive to the anti-KDR/Flk-1 antibody. Lumiglo is a proprietory mixture of reagents containing a substrate which is converted to a chemiluminescent compound by the action of horseradish peroxidase. The light from this is detected by photographic film, for example Kodak Biomax ML.

The invention claimed is:

1. An isolated antibody generated using a peptide consisting of SEQ ID NO: 1 or SEQ ID NO: 2 as an immunogen.

2. The antibody of claim 1, wherein the antibody is a monoclonal antibody.

3. The antibody of claim 1, wherein the antibody is a polyclonal antibody.

4. A composition comprising the antibody of claim 1 and a carrier.

5. A kit for detecting the activation of KDR/Flk-1 comprising the antibody of claim 1 and reagents for a detection assay.

6. The antibody of claim 1, wherein the antibody is a F(ab')$_2$, a Fab, or a single chain Fv.

7. A method of generating an antibody, comprising immunizing an animal with a peptide consisting of SEQ ID NO: 1 or SEQ ID NO: 2, and isolating the antibody from the animal.

8. The method of claim 7, wherein the animal is a mammal.

9. An isolated antibody generated by the method of claim 7.

10. An isolated antibody that binds to a peptide consisting of SEQ ID NO: 1 or SEQ ID NO: 2.

11. A method for detecting the presence of KDR/Flk-1 comprising mixing the antibody of claim 1 with a biological sample to detect the presence of KDR/Flk-1.

12. A method for measuring the amount of KDR/Flk-1 in a sample comprising mixing the antibody of claim 1 with a biological sample and measuring the amount of KDR/Flk-1 in the sample.

13. The method of claim 12, wherein measuring the amount of KDR/Flk-1 in the sample comprises performing an assay selected from the group consisting of a fluorimetric assay, a chromogenic assay, a radiolabelled assay, and a chemiluminescence assay.

* * * * *

```
                        SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: 14aa sequence from human KDR receptor
      phosphorylated on tyrosine with N terminal acetyl group and C
      terminal amide
<220> FEATURE:
<221> NAME/KEY: MOD_RES
<222> LOCATION: (1)..(1)
<223> OTHER INFORMATION: Xaa at position 1 is N-acetylcysteine
<220> FEATURE:
<221> NAME/KEY: MOD_RES
<222> LOCATION: (7)..(7)
<223> OTHER INFORMATION: Xaa at position 7 is O-phosphonotyrosine
<220> FEATURE:
<221> NAME/KEY: MOD_RES
<222> LOCATION: (14)..(14)
<223> OTHER INFORMATION: Xaa at position 14 is serinamide

<400> SEQUENCE: 1

Xaa Asp Pro Lys Phe His Xaa Asp Asn Thr Ala Gly Ile Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: 14aa sequence from human KDR receptor with N
      terminal acetyl group and C terminal amide
<220> FEATURE:
<221> NAME/KEY: MOD_RES
<222> LOCATION: (1)..(1)
<223> OTHER INFORMATION: Xaa at position 1 is N-acetylcysteine
<220> FEATURE:
<221> NAME/KEY: MOD_RES
<222> LOCATION: (14)..(14)
<223> OTHER INFORMATION: Xaa at position 14 is serinamide

<400> SEQUENCE: 2

Xaa Asp Pro Lys Phe His Tyr Asp Asn Thr Ala Gly Ile Xaa
1               5                   10
```